United States Patent
Ballato et al.

(10) Patent No.: US 7,193,352 B1
(45) Date of Patent: Mar. 20, 2007

(54) THIN FILM BULK ACOUSTIC WAVE SENSOR SUITE

(75) Inventors: Arthur Ballato, Oceanport, NJ (US); Richard H. Wittstruck, Howell, NJ (US); Xiaojun Tong, WuXi (CN); Yicheng Lu, East Brunswick, NJ (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 182 days.

(21) Appl. No.: 11/081,894

(22) Filed: Mar. 11, 2005

(51) Int. Cl.
*H01L 21/08* (2006.01)
*H03H 9/12* (2006.01)

(52) U.S. Cl. .................................. 310/320
(58) Field of Classification Search ............... 310/311, 310/800
See application file for complete search history.

(56) References Cited

U.S. PATENT DOCUMENTS

| | | | | |
|---|---|---|---|---|
| 5,936,150 | A * | 8/1999 | Kobrin et al. | 73/24.06 |
| 6,196,059 | B1 * | 3/2001 | Kosslinger et al. | 73/61.49 |
| 6,995,497 | B2 * | 2/2006 | Inoue | 310/320 |
| 2006/0210440 | A1 * | 9/2006 | Potyrailo et al. | 422/82.01 |

FOREIGN PATENT DOCUMENTS

WO  WO-2005-036150  *  4/2005

OTHER PUBLICATIONS

Gerber, Eduard A. and Ballato, Arthur, Precision Frequency Control, vol. 1, Acoustic Resonators and Filters, Academic Press, Inc., 1985, pp. 279-284.
Schreve, William R. and Cross, Peter S. pp. 118-145.
Ballato, Arthur et al, "Lateral Field Equivalent Networks and Piezocoupling Factors of Quartz Plates Driven in Siple Thick-ness Modes", IEEE Transactions on Ultrasonics, Ferroelectrics, and Frequency Control, vol. UFFC-33, No. 4, Jul. 1986, pp. 385-393.
Smith, W. Richard et al, "Analysis of Interdigital Surface Wave Transducers by Use of an Equivalent Circuit Model", IEEE Transactions on Microwave Theory and Techniques, vol. MTT-17, No. 11, Nov. 1969, pp. 856-864.
Ballato, Arthur, "Analog Network Representation of Interdigital Surface Wave Transducers", R&D Technical Report, ECOM 4322, May 1975, pp. 1-7.
Lakin, K.M., "Thin Film Resonators and Filters", IEEE Ultra-sonics Symposium, 1999, pp. 895-906.
Seabury, C.W. et al, "Thin Film ZnO Based Bulk Acoustic Mode Filters", IEEE MTT-S Digest, 1997, pp. 181-184.

* cited by examiner

*Primary Examiner*—Thomas M. Dougherty
(74) *Attorney, Agent, or Firm*—Michael Zelenka; George B. Tereschuk

(57) ABSTRACT

Thin film bulk acoustic wave sensors with coatings of biological and chemical materials, multiple electrode depositions and a piezo-active thin film transducer layer are hosted on a substrate. The thin film bulk acoustic wave sensor suite, or T-BASS, produces a low-voltage, IC-compliant thickness-directed electric field that is substantially uniform over a substantial portion of the active area of the BAW structure. The BAWs produced are essentially extensional plane waves propagating away from the substrate surface and having phase progression substantially oblique to the substrate surface. For BAW applications requiring sensing by an active layer, it would be most desirable to have an electrode structure that is both IC-compliant and can be energized from a low-voltage source of electrical energy. The thin film BAW sensors are compatible with IC fabrication and processing techniques, such as photolithography. Both single channel and multiple channel thin film bulk acoustic wave sensors are provided.

20 Claims, 8 Drawing Sheets

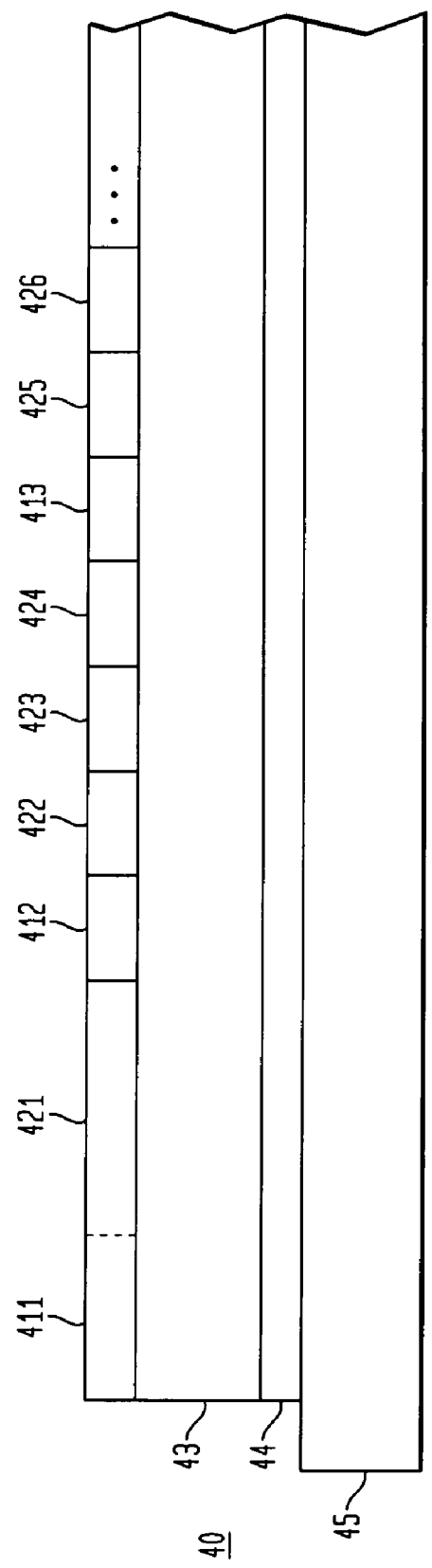

THIN FILM BULK ACOUSTIC WAVE SENSOR SUITE

GOVERNMENT INTEREST

The invention described herein may be manufactured, used, imported, sold, and licensed by or for the Government of the United States of America without the payment to us of any royalty thereon.

FIELD OF THE INVENTION

This invention relates in general to field of solid-state acoustic devices. In particular, this invention relates to a Thin Film Bulk Acoustic-Wave Sensor Suite.

BACKGROUND OF THE INVENTION

Bulk Acoustic Waves (BAWs) are generated in piezoelectric media by applying a time-varying electric source to a suitable electrode system. Often the source can be a sinusoidal or quasi-sinusoidal voltage. The electrode system varies according to the forms of the piezoelectric body, and the ensuing motion intended. Over the years, many shapes and modes of motion have been employed. Piezoelectric materials have been used either as a single body, or suitably attached to other substances to form composite shapes that yield the desired structure. The desired structure may comprise rods and bars, rectangular and circular plates, forks and so on. When used as an acoustic resonator or filter, one or more frequency-determining dimensions of the body are employed to yield the desired resonance characteristics. When used as a sensor, piezoelectric materials are exposed in aqueous solution measuring the loading effects from ambient molecules adhering to the device's surface.

One simple example of using a piezoelectric material as a sensor is a thin plate comprised of a single piezoelectric material with electrodes placed upon the major surfaces. When an electric voltage energizes the plate and the requisite piezoelectric coefficient exists, the plate will exhibit resonances when the exciting frequency is such that its thickness dimension is an integral multiple of an acoustic wavelength. In this situation, BAWs form standing wave patterns in the thickness direction; the standing wave pattern is comprised of two counter-propagating waves, each traveling in the thickness direction. As sensing ensues, the mass loading of the in situ solution constituents results in shifts in the resonant frequency spectrum that can be interpreted as "signatures" of the element's concentration in the solution.

Progression of sensing technology with time has been toward operation at increasingly higher frequencies and this tendency is apt to continue in the near future. Wavelength is inversely proportional to frequency, so one therefore finds increasing use of the thickness of piezoelectric materials as the frequency-determining dimension for BAWs. The structures take the forms of thin films and membranes in order to reach the high frequencies demanded by technological needs. Mechanical motions of this nature are referred to as thickness modes of vibration.

There are two primary methods of exciting BAWs in plates and other structures, and they differ in the direction of the exciting electric field. In one method, the exciting electric field is parallel to the direction of propagation of the acoustic waves, while in the other; the exciting electric field is perpendicular to the direction of propagation of the acoustic waves. When applied to the thickness modes of a plate, the acoustic plane waves propagate in the thickness direction; when electrodes are placed on the major surfaces of the plate, the exciting field is in the thickness direction. This excitation method is consequently called "thickness excitation" (TE) or "thickness-field excitation" (TFE). Electrodes placed at the plate edges to produce a field in a direction parallel to the plate surface, and hence perpendicular to the acoustic plane wave direction, produce what is referred to as "lateral excitation" (LE) or "lateral-field excitation" (LFE).

Another type of acoustic mode is the surface acoustic wave (SAW) and there are several varieties of these, the most often used is the Rayleigh surface wave. This type of wave has motion that is primarily confined within an acoustic wavelength or two of the surface of a planar structure, and propagates in a direction lateral to the depth of the substrate, i.e., in a direction along the planar surface.

When the SAW mode was first exploited in electronic technology, various methods were used to generate the SAW waves. One technique is to attach a BAW wave transducer to one slanted face of a prism bonded to a planar surface upon which it is desired to propagate the SAW. The BAW impinging on the surface at an angle converts a portion of its energy to a SAW, which then propagates along this surface, in the direction away from the prism.

Introduction of the interdigital transducer (IDT) resulted in an efficient method for generating SAWs. The IDT, moreover, is a planar electrode structure that can be applied by highly developed methods, such as photolithography, that are used in the microelectronics industry. The IDT has become the transduction means of choice for SAW applications, and has been developed in a variety of configurations depicted in FIGS. 1 and 2.

Referring now to FIGS. 1A–1C, the simplest IDT consists of two symmetrically interdigitated combs of identical electrode finger stripes, each comb consisting of geometrically parallel metallic fingers. FIG. 1A is a perspective view of an IDT piezoelectric plate 10, comprising a substrate 11, input transducer 12, input terminal pair 13 and 14, SAW, represented by wiggly line 15, output transducer 16 and output terminal pair 20 and 21. Arrow 17 indicates the preferred direction of propagation in the piezoelectric plate. The FIG. 1B cross-sectional view of substrate 11 depicts two sets of three finger pairs of IDT electrode fingers stripes 18 for illustrative purposes. The typical IDT generally includes hundreds of finger pairs. The FIG. 1C exploded view depicts one pair, or period 19, of IDT finger stripes 18 and a period gap, or separation, G, between the IDT fingers 18. The FIG. 1C width A between the centers of each IDT finger 18 is ½ λ, and the width of each IDT finger 18 is ¼λ, where λ is the acoustic wavelength, equal to the SAW velocity divided by the frequency of operation. Aluminum is often preferred as the electrode finger material because its acoustic impedance closely matches the acoustic impedances of most piezoelectric substrates. The IDT piezoelectric plate 10 depicted in FIGS. 1A–1C is a two-port structure, and the exciting voltage is placed across the two bus bars to energize the electrode fingers.

FIGS. 2A–2F depict a number of well-known IDT concepts and configurations. FIG. 2A illustrates a typical SAW configuration; the number of electrode fingers and transducer separation is related to bandwidth. FIG. 2B illustrates an alternative SAW configuration; where the number of fingers per period, or wavelength, is varied. FIGS. 2C and 2D illustrate a thinned transducer, or open structure, and dummy fingers, respectively. FIG. 2E depicts one and two port configurations. FIG. 2F depicts the concept of apodization in which changing the overlap of the fingers from opposite electrodes in a determined pattern results in weighting the frequency response of the transducer.

Another advantage of the IDT for SAW applications, is that the frequency characteristics, such as center frequency of a resonator and bandwidth of a filter are determined by the dimensions of the IDT, rather than the dimensions of the piezoelectric structure. This allows reaching high frequencies by photolithographic means on a robust substrate, rather than by reducing the thickness of a plate.

Despite the advantages of SAW operation briefly mentioned, for many applications BAW devices are preferable to SAW devices. Prior art BAW and SAW sensors that have relied upon the inclusion of a biologically active or chemically active layer, hereinafter bio-active or chem-active layer, respectively, specific to an antigen or chemical to be detected in an ambient environment. SAW sensors also present fabrication difficulties because two parallel, planar IDTs are required, with one IDT as a reference arm and the other IDT as a detection arm coated with a bio-active or chem-active layer. The prior art parallel IDT design is complex in both mask design and processing, because selective deposition of the active layer requires careful consideration so as not to corrupt the reference arm surface. Although BAW devices are generally simpler to design and fabricate, they have also demonstrated limitations as ambient mass loading, usually due to nonspecific binding agents, such as liquid or vapor phase water, that have reduced the sensitivity of these devices to a specific antigen or agent. Therefore, prior art BAW and SAW sensing arrangements are inadequate because of their reliance upon a specific a bio-active or chem-active layer for the substance of interest and the inherent complexities of the dual IDT parallel approach. Up until now, BAW quartz crystal microbalances (QCMs) using piezoelectric crystals as host assemblies for transducing the acoustic waves, (i.e., piezo-driving the acoustic waves) and substrate media for the bio-active or chem-active layers have been used for sensing bio-active and chem-agents, but the QCM is not always suitable because the bio-active or chem-agents usually do not selectively bind to the electrode material. To date, SAW devices have seen increasing use in the commercial world despite their sensitivity and processing limitations, and BAW sensors have languished due to traditional designs being unable to overcome the nonspecific mass-loading characteristic of such devices.

Additionally, there are a number of other difficulties to overcome in producing electrode structures for thickness shear, or extensional, excitation of BAW. One major difficulty is including a thin film active layer capable of bonding to select piezoelectric material major surfaces. Another limitation is the ability to augment the electrode to accommodate two or more channels for both detection and reference operation. Another problem in this area is the ability to operate at higher frequency regions (i.e., GHz). Up until now, BAWs generated from IDTs would be considered weak, spurious and detrimental because the typical low IC (integrated circuit) voltages do not provide adequate electric field strength for piezoelectric excitation of conventional electrode structures and result in unacceptable performance. Additionally, a non-uniform electric field further degrades performance. Traditional BAW sensors operate with phase progression perpendicular to the substrate surface and ambient solution mass loading tends to dampen the sensing response.

To overcome the disadvantages, shortcomings and limitations of prior art BAW sensors, a new BAW structure needs to exhibit a number of characteristics. The new BAW structure should produce BAWs that are essentially extensional plane waves, with propagation away from the substrate surface and phase progression substantially oblique to the substrate surface. This is a critical because prior art BAW sensors operate with phase progression substantially perpendicular to the substrate surface and mass loading (i.e., from an ambient solution) dampens the sensing response. The new BAW sensor structure should also produce a thickness electric field that is substantially uniform over a substantial portion of the structure's active area to virtually eliminate the sharp spikes depicted in FIGS. 3, 4, and 5, arising from the IDT structure, and mitigate the spurious readings from SAW sensors. The new BAW sensor structure should have a low voltage electric field that can be produced with the low voltages of around 10 volts or less typically found in integrated circuit (IC) chips.

Up until now, there has been a long-felt need for BAW sensors to overcome the disadvantages, shortcomings and limitations of reliance upon a specific active layer for the substance of interest, nonspecific mass loading and the inherent complexities of the dual IDT (parallel) approach. This invention fulfills this long-felt need with a BAW sensor structure coated with biological and/or chemical materials with multiple electrode depositions and a thin film piezo-transduction layer hosted on a substrate. By employing suitably placed coatings of biological or/and chemical active material, along with multiple electrode depositions that preserve the extensional wave propagation, on a thin film piezo-transduction layer hosted on a substrate the disadvantages, shortcomings and limitations of the prior art have largely been overcome and obviated. The BAW sensor structure of the present invention produces a low-voltage, substantially thickness-directed electric field and BAWs that are essentially extensional plane waves propagating away from the substrate surface having a phase progression substantially oblique to the substrate surface. The low-voltage, thickness-directed electric field produces essentially extensional BAWs that are also substantially uniform over a substantial portion of the BAW structure. Furthermore, the new BAW structure of the present invention is also compatible with IC processing techniques.

SUMMARY OF THE INVENTION

It is an object of the present invention to provide thin film BAW wave sensors producing a substantially thickness-directed electric field.

It is another object of the present invention to provide a thin film BAW sensor structures that produce a thickness-directed electric field and extensional plane wave BAWs.

It is still a further object of the present invention is to provide a thin film BAW sensor coated with biological and chemical materials, having multiple electrode depositions and a thin film piezo-transduction layer hosted on a substrate to produce a low-voltage, thickness-directed electric field and BAWs that are essentially extensional plane waves propagating away from the substrate surface having a phase progression substantially oblique to the substrate surface, without suffering from the disadvantages, shortcomings and limitations of prior art BAWs.

It is yet another object of the present invention is to provide methods of detecting a concentration of unknown substances on a piezoelectric material by generating a low-voltage, thickness-directed electric field and bulk acoustic waves with a bulk acoustic wave sensor.

These and other objects and advantages are provided by this invention's BAW sensor having coatings of biological and chemical materials, multiple electrode depositions and a thin film piezo-transduction layer hosted on a substrate. The thin film bulk acoustic wave sensor suite, or T-BASS, produces a low-voltage, IC-compliant thickness-directed electric field that is substantially uniform over a substantial portion of the active area of the BAW structure. The BAWs produced in accordance with the present invention are essentially extensional plane waves propagating away from the substrate surface and having phase progression substantially oblique to the substrate surface. The ability to generate extensional plane waves with a phase progression component along the substrate surface is an important feature of the present invention because prior art BAW sensors operate with phase progression perpendicular to the substrate surface. The configuration of the thin film BAW sensor also overcomes the prior art limitation of mass loading the ambient solution to dampen the sensing response. For BAW applications requiring sensing by an active layer, it would be most desirable to have an electrode structure that is both IC-compliant and can be energized from a low-voltage source of electrical energy. And, the thin film BAW sensors are compatible with IC fabrication and processing techniques, such as photolithography.

BRIEF DESCRIPTION OF THE DRAWINGS

FIG. 7C is a conceptual cross-sectional view of an embodiment of the multiple channel sensor suite of the present invention.

DETAILED DESCRIPTION OF THE DRAWINGS

The present invention provides a thin film BAW sensor suite, or T-BASS, structure to overcome the disadvantages, shortcomings and limitations of prior art BAWs. The thin film BAW sensors advantageously provide an innovative crystalline orientation providing essentially extensional plane waves propagating away from the substrate surface and having phase progression substantially oblique to the substrate surface in the thickness direction. The term "thin film" is defined as a layer, of substantially constant thickness, that has dimensions lateral to the thickness of at least 20 to 50 thicknesses, and which is usually deposited on a robust substrate for mechanical support. In the additional sense used herein, it is a layer of piezoelectric material whose thickness is such as to be capable of generating acoustic waves in the MHz to GHz range. The thin film BAW sensor structures further comprise biological and chemical coatings, multiple electrode depositions and a thin film piezo-transduction layer hosted on a substrate to producing BAWs that are essentially extensional plane waves, with propagation away from, but with phase progression substantially oblique to, the substrate surface. These thin film BAW sensors are energized by a low-voltage, thickness-directed electric field that is substantially uniform over a substantial portion of the active area of the BAW structure and compatible with IC processing techniques. The thin film BAW sensor structures of the present invention efficiently generate BAWs and simultaneously discriminates against nonspecific binding agents to a significant extent. The present invention contemplates a single channel thin film BAW sensor, a multiple channel thin film BAW sensor and methods of detecting a concentration of unknown substances on a piezoelectric material by generating a low-voltage, thickness-directed electric field and bulk acoustic waves with a bulk acoustic wave sensor.

Figure 1A:
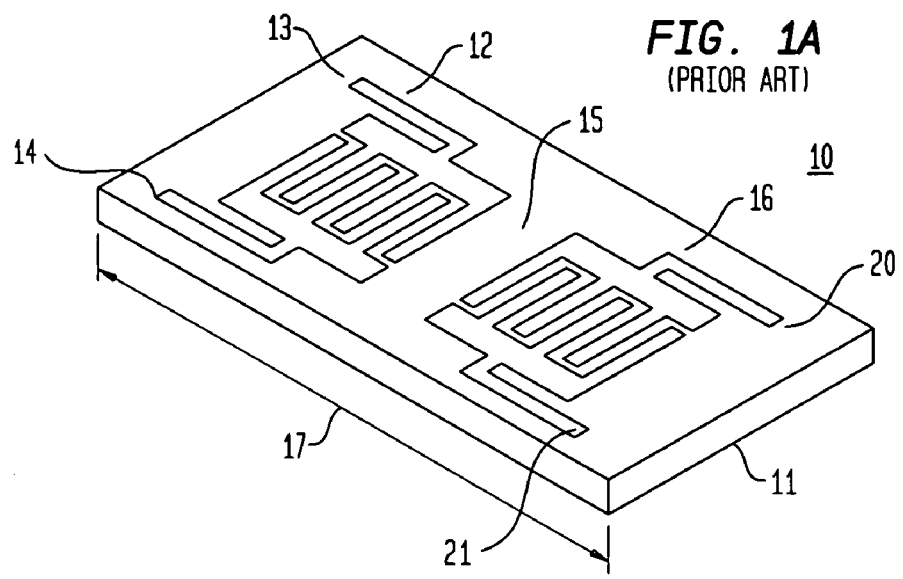
FIGS. 1A–1C are perspective, cross-sectional and exploded views of a prior art interdigital transducer.
Figure 1B:
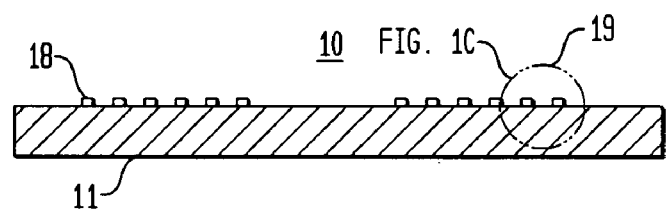
Figure 1C:
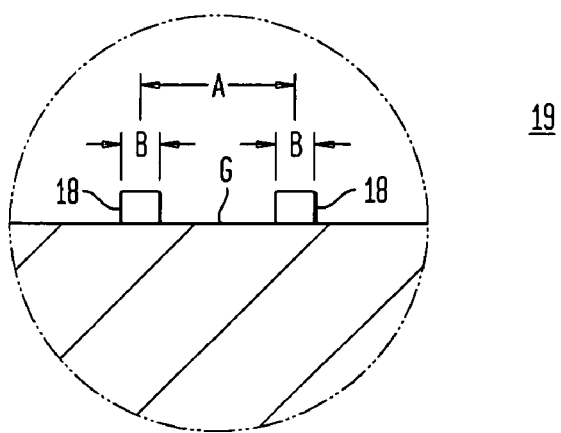
Figure 2A:
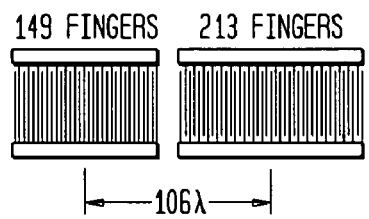
FIGS. 2A–2F are examples prior art IDT interdigital transducer configurations.
Figure 2B:
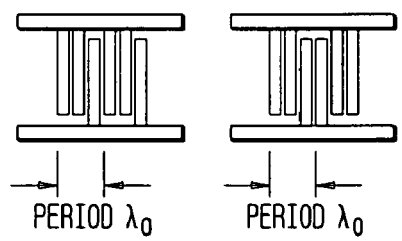
Figure 2C:
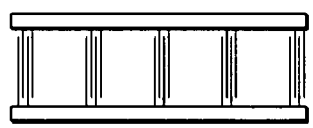
Figure 2D:
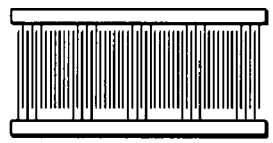
Figure 2E:
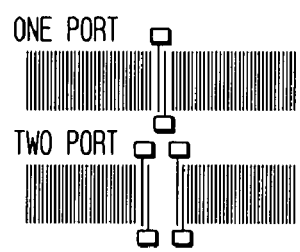
Figure 2F:
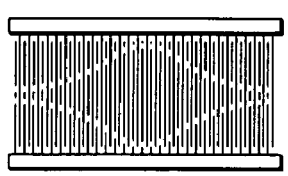
Figure 3:
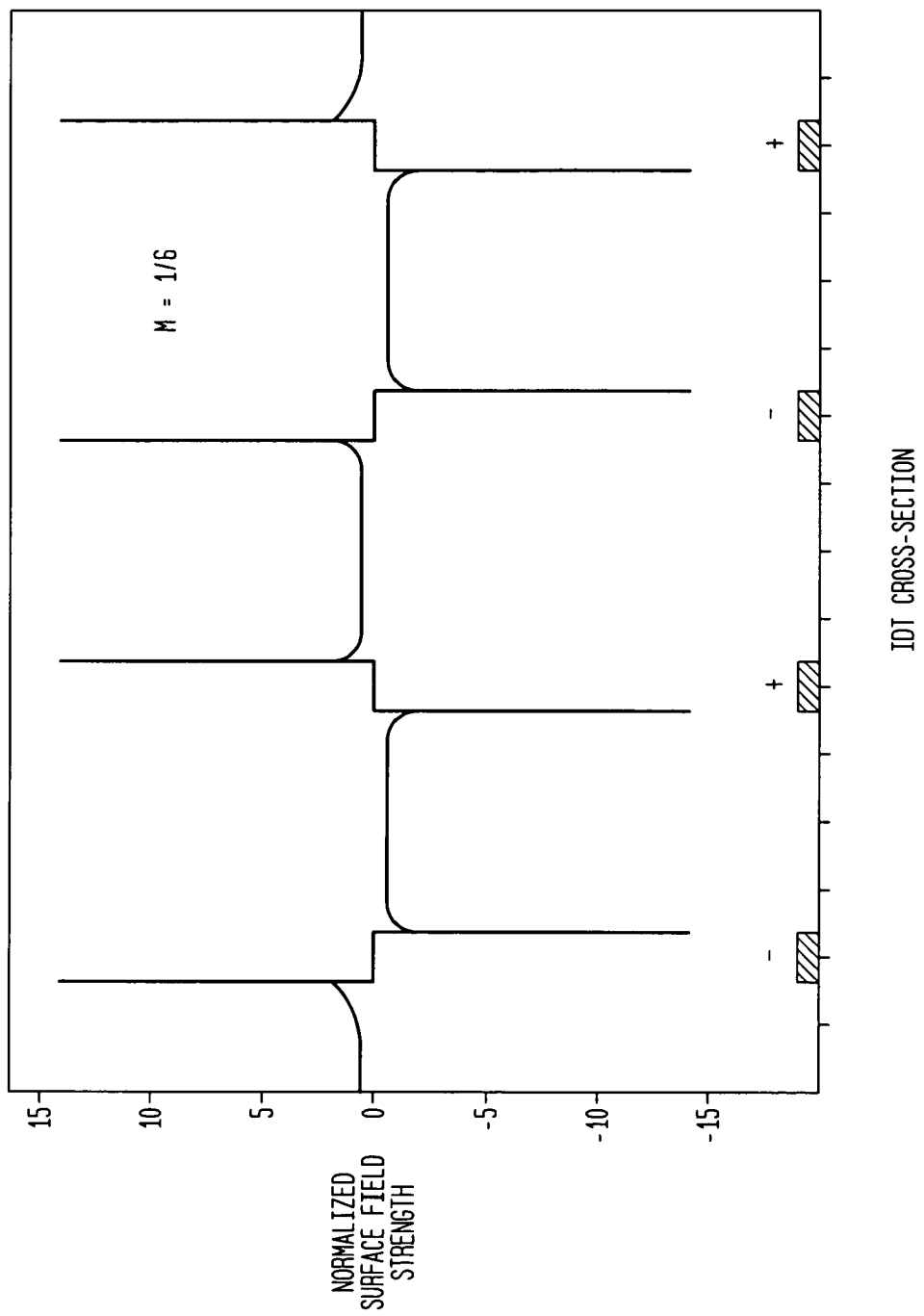
FIG. 3 is a graph plotting e along the gaps for a metallization ration of m=⅙.
Figure 4:
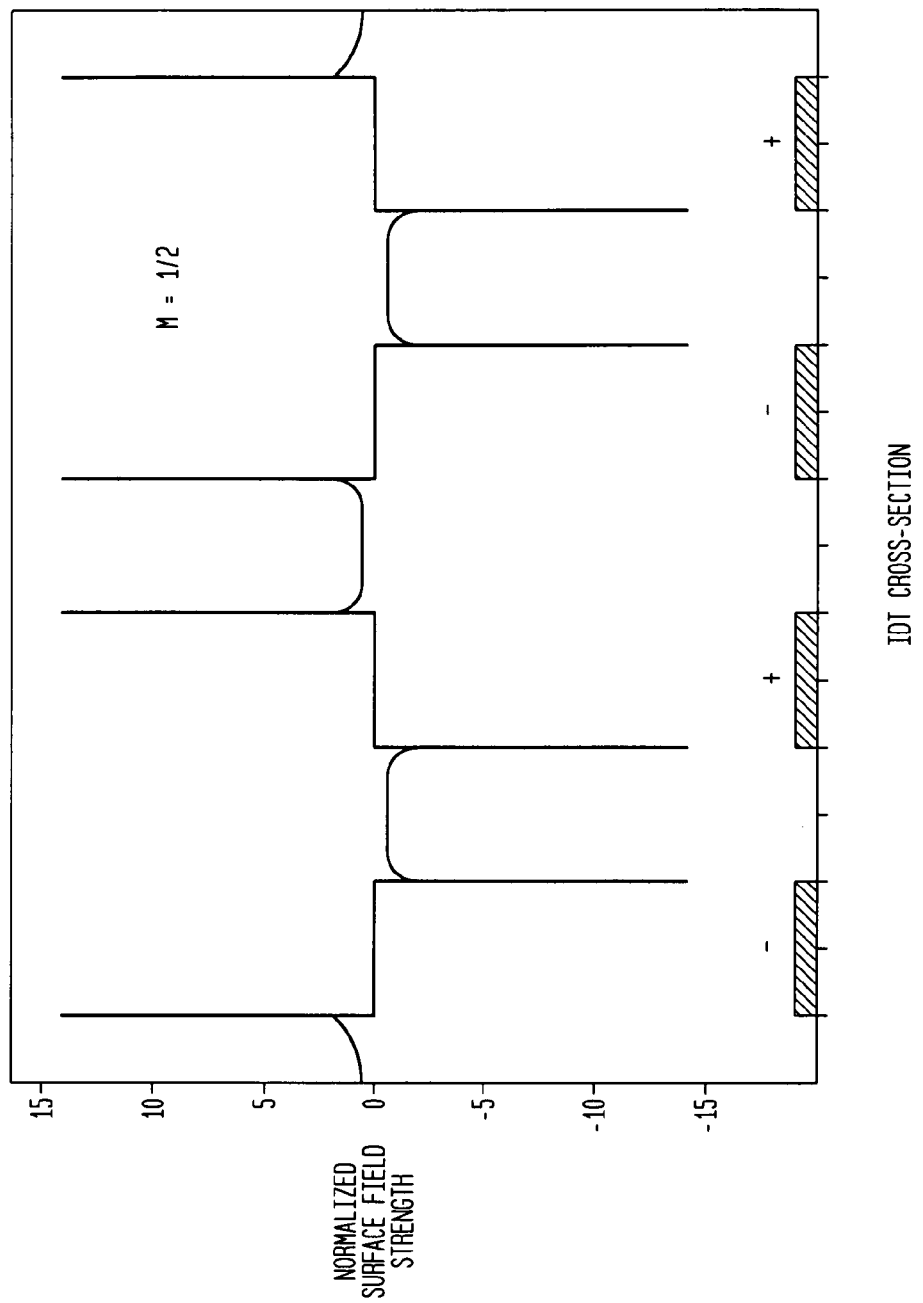
FIG. 4 is a graph plotting e along the gaps for a metallization ration of m=½.
Figure 5:
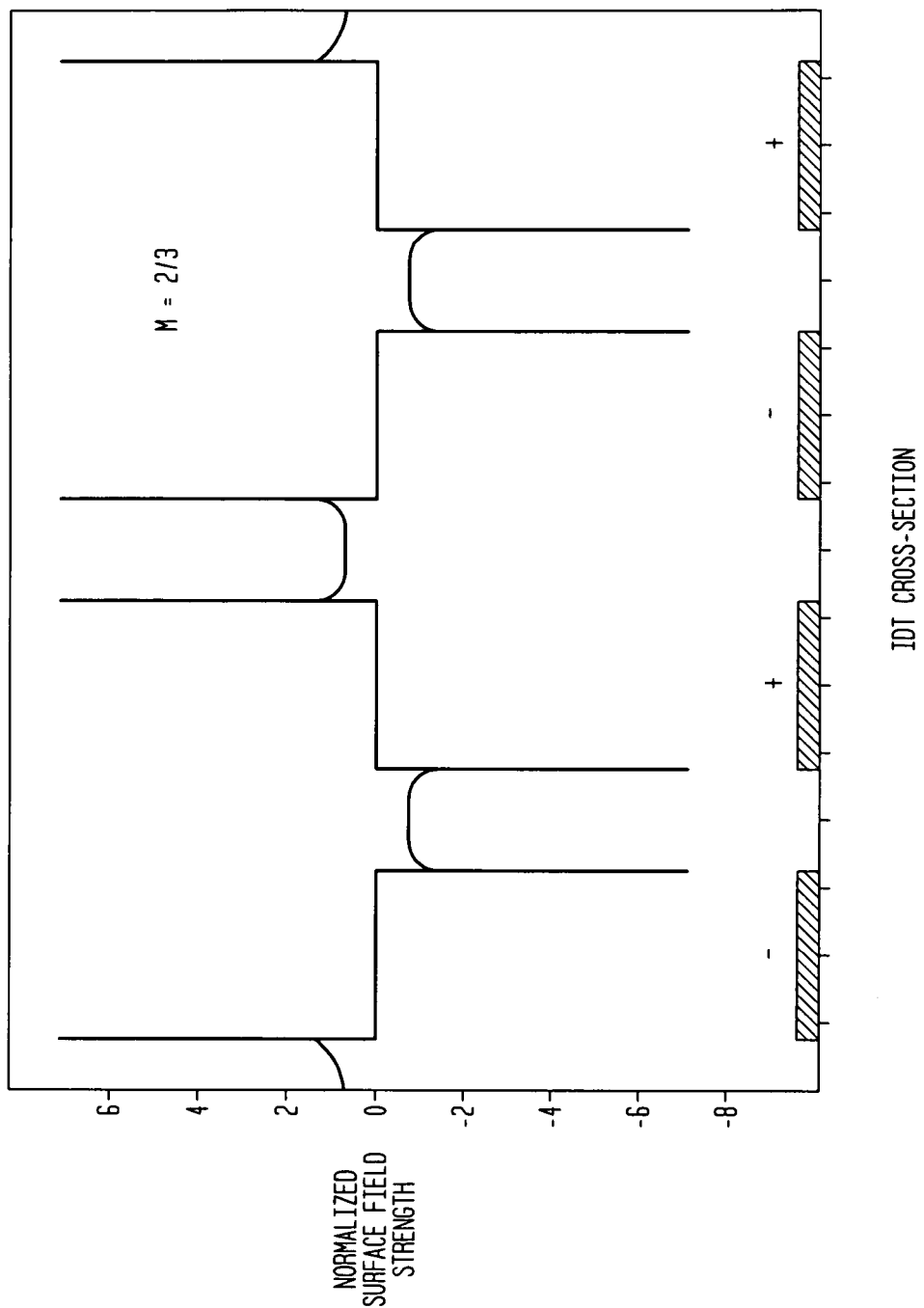
FIG. 5 is a graph plotting e along the gaps for a metallization ration of m=⅔.

Referring now to the drawings, FIG. 3 is a chart plotting, in crossectional view, the normalized electric field strength e ($\psi$, m) along the gaps of an IDT with a metallization ratio where m=⅙. FIG. 4 is a similar chart plotting e along the gaps with a metallization ratio where m=½. FIG. 5 is a similar chart plotting e along the gaps with a metallization ratio where m=⅔. The charts illustrate how the electric field strength peaks sharply in the vicinity of each electrode edge. These peaks, and the corresponding ones arising from the normal component of the electric field, lead to the interpretation of the piezoelectric tractions as Dirac delta functions placed at the electrode edges. Sharp spikes of electric field strength, as depicted in FIGS. 3, 4, and 5, arise from the thin edges of the electrodes. Those skilled in the resonator arts will quickly recognize that such high fields are a general phenomenon associated with metallic geometries having small curvatures, such as points, edges and other uneven surface characteristics. These high fields are inimical to the operation of BAW structures, and to many electronic components as well.

Figure 6A:
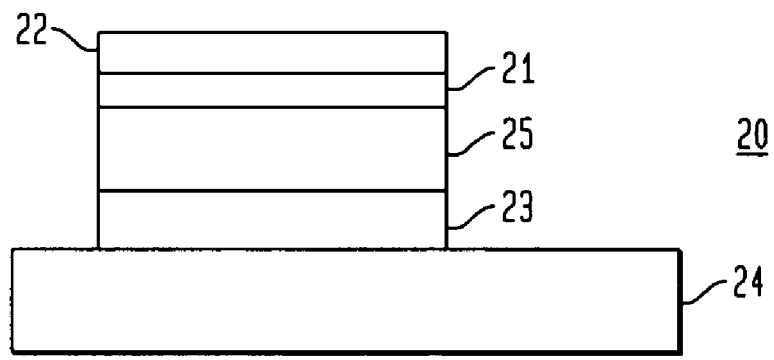
FIG. 6A is a conceptual cross-sectional view of the single channel sensor suite embodiment of the thin film bulk acoustic wave sensor of the present invention.
Figure 6B:
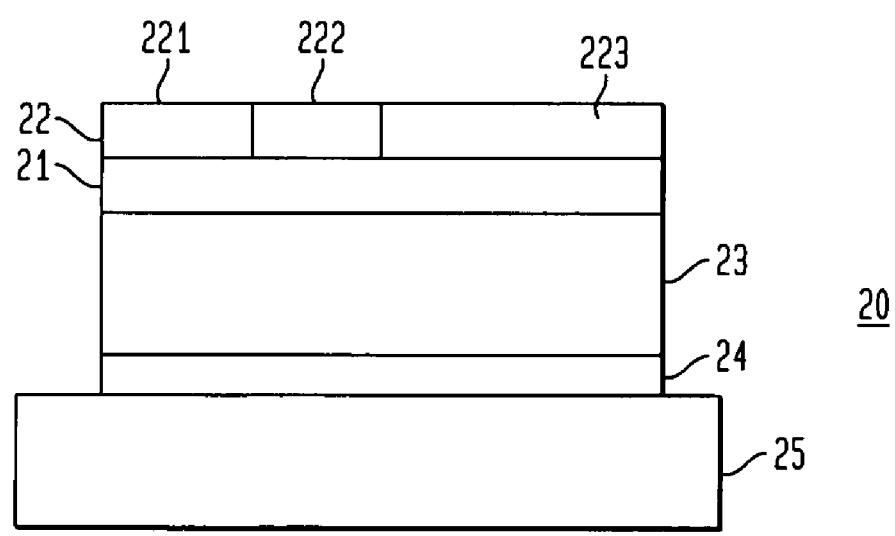
FIG. 6B is a conceptual cross-sectional view of another single channel sensor suite embodiment of the thin film bulk acoustic wave sensor of the present invention.

Referring now to FIG. 6A, there is depicted a conceptual cross-sectional view of a single channel thin film BAW sensor 20 of the present invention, comprising a substrate 24, a bottom electrode 23, a piezo-active thin film transducer 25, a top electrode 21, and an active layer 22 further comprising one or more bio-active or chem-active coatings. The critical element of the single channel thin film BAW sensor 20 of the present invention is the active layer 22. The active layer 22 of FIG. 6A may comprise an array of active coatings of biological and chemical materials, capable of concurrently sensing multiple antigens or agents, as depicted in FIG. 6B, wherein active layer 22 further comprises an array of bio-active or chem-active elements 221, 222 and 223. For example, the active layer 22 array could include carbon and polymer based bio-active materials, fluorescin-doped antibodies, oligonucleotides and enzymes, which are capable of sensing a wide variety of bio-active and chemical-agents.

In operation, active layer 22 array provides a thin film piezo-transduction layer hosted on substrate 25 to produce BAWs that are essentially extensional plane waves, with propagation away from the surface of substrate 25 and a phase progression substantially oblique to the surface of substrate 25. This oblique progression arises because of a lateral variation introduced in the areal mass of active layer array 22, which tilts the propagation angle of the BAWs. The single channel thin film BAW sensor 20 efficiently generates BAWs and simultaneously discriminates against nonspecific binding agents to a significant extent. Substrate 25 can be an inert substance, such as sapphire, that supports the entire structure.

FIGS. 6A and 6B may appear to be somewhat similar to a QCM in that the detection takes place above the upper electrode. In the classical QCM, the adherent species attaches directly to the electrode. In the structures depicted in FIGS. 6A and 6B, on the other hand, the measurand (i.e., the adherent species) attaches to the active layer 22 because of its bio-active or chem-active properties. A number of variations of the single channel thin film BAW sensor are possible, including the sensor 20 being fabricated with integrated circuit processing techniques.

Figure 7A:
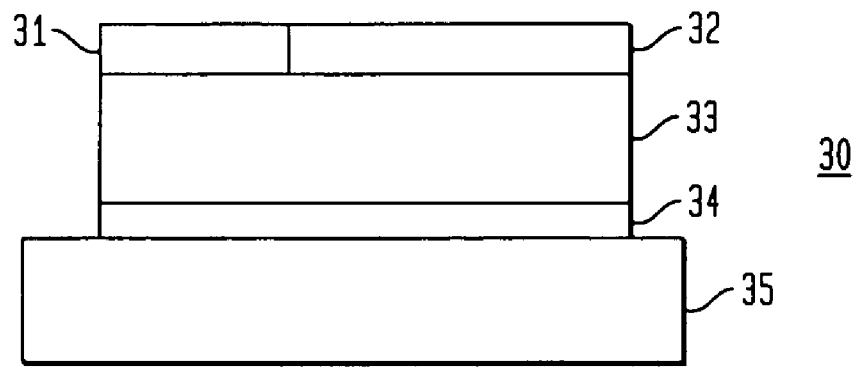
FIGS. 7A–7B are conceptual cross-sectional views of alternative embodiments of the single channel sensor suite of the present invention.
Figure 7B:
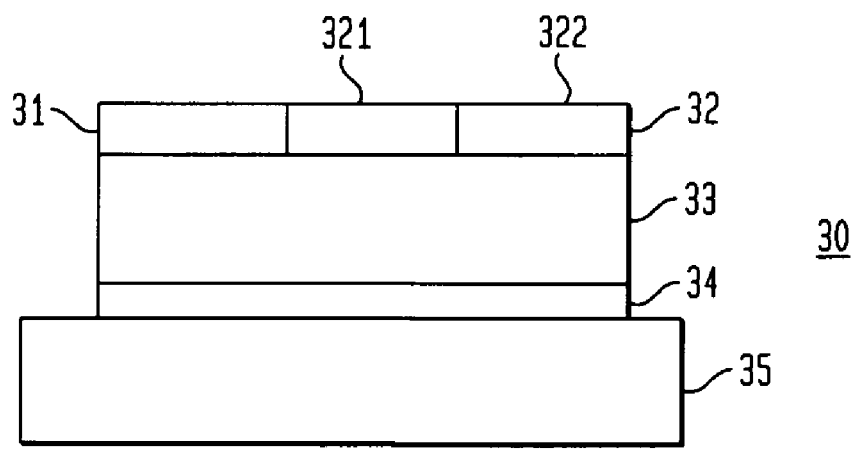

FIG. 7A is a cross-sectional view of a preferred embodiment of the single channel thin film bulk acoustic wave sensor 30 of the present invention comprising a first electrode 31 deposited next to a bio-active or chem-active layer array 32, both of which are stacked on a piezoelectric material 33, (i.e., a thin film piezo-transduction layer) that is stacked on a second electrode 34 and a substrate 35. Similar to the single channel thin film bulk acoustic wave sensor 20, the critical element in this single channel thin film bulk acoustic wave sensor 30 is that the active layer array 32 that is now placed laterally adjacent to the first electrode 31 instead of atop the first electrode 31. This feature makes the fabrication of the device compatible with integrated planarization techniques. The active layer 32 of FIG. 7A may comprise an array of active coatings of biological and chemical materials, capable of concurrently sensing multiple antigens or agents, as depicted in FIG. 7B, wherein 32 is comprised of two bio-active or chem-active elements 321 and 322.

FIG. 7C is an embodiment of a multiple channel sensor suite 40, comprising a top electrode array with elements 411, 412 and 413 interspersed with, and laterally adjacent to, a bio-active or chem-active array, with elements 421, 422, 423, 424, 425 and 426, all of which elements are stacked on a piezoelectric material 43, (i.e., a thin film piezo-transduction layer) that is stacked on a second electrode 44 and a substrate 45. The electrode array 411–413 and laterally adjacent bio-active or chem-active array 421–426 have their elements interspersed, as shown, in various combinations. The electrode array elements 411, 412 and 413, may all have different voltages and electrical phases for the purpose of producing an oblique component of the BAW to interrogate the elements of the laterally adjacent bio-active or chem-active array elements 421, 422, 423, 424, 425 and 426. The array of active layers is capable of concurrently sensing multiple antigens or agents. For example, the array could include carbon and polymer based bio-active materials, fluorescin-doped antibodies, oligonucleotides and enzymes, which are capable of sensing a wide variety of bio-active and chemical-agents.

This multiple channel embodiment also provides many of the advantages of the single channel embodiment, including efficient propagation of bulk acoustic extensional mode waves, with the first and second electrodes 41A–C and 44 being configured in structures that are compatible with IC processing techniques, such as photolithography. In operation, the multiple channel thin film BAW sensor 40 of the present invention generates a low-voltage, thickness-directed electric field that is substantially uniform over a substantial portion of the active area of the BAW structure. The structure of this invention's multiple channel thin film BAW sensor 40 is also compatible with IC processing techniques including multilevel photolithography and planarization techniques, which are both widely used in the microelectronics industry. The BAWs are essentially extensional plane waves, with propagation away from, but with phase progression substantially oblique to, the surface of substrate 45.

The present invention also encompasses methods of detecting a concentration of unknown substances on a piezoelectric material by generating a low-voltage, thickness-directed electric field and bulk acoustic waves with a bulk acoustic wave sensor, comprising the steps of selecting the piezoelectric material forming a first electrode and a second electrode, forming a bio-active or chem-active layer array with a plurality of identifying biological and/or chemical materials, aligning the first electrode and bio-active or chem-active layer array together, forming a substrate and stacking the second electrode on the substrate. Other steps of this method are producing a low-voltage, thickness-directed electric field from said BAW sensor, said electric field being substantially uniform over a portion of said active area, exciting a extensional plane bulk acoustic wave from the piezoelectric material propagating away from the active area and providing a phase progression substantially oblique to the active area and simultaneously discriminating against nonspecific binding agents from the concentration, reducing a plurality of electrode field intensity spikes with the bulk acoustic wave and concurrently identifying a plurality of chemical compositions of said concentration of unknown substances based upon said plurality of nonspecific modes.

Many of the variations of the single channel thin film BAW sensor and multiple channel thin film BAW sensor are also applicable to these methods.

What is claimed is:

1. A thin film bulk acoustic wave sensor, comprising:
   a first electrode and an active layer are positioned on a piezo-active thin film transducer;
   said transducer being placed on a second electrode that is stacked on a substrate with a top surface;
   said active layer, having an array of biological and chemical identification materials, contacts a concentration of unknown substances and produces a low-voltage, thickness-direction electric field that excites an extensional plane bulk acoustic wave;
   said extensional plane bulk acoustic wave propagates away from said top surface, produces a phase progression substantially oblique to said top surface and simultaneously discriminates against a plurality of nonspecific binding modes from said concentration; and
   said plurality of nonspecific modes and said plurality of identification materials identify said concentration.

2. The thin film bulk acoustic wave sensor, as recited in claim 1, further comprising:
   said first electrode being a top electrode; and
   said second electrode being a bottom electrode.

3. The thin film bulk acoustic wave sensor, as recited in claim 2, further comprising:
   said array of biological and chemical identification materials being selected from the group consisting of carbon and polymer based bio-active materials, fluorescin-doped antibodies, oligonucleotides and enzymes; and
   said substrate being composed of an inert material.

4. The thin film bulk acoustic wave sensor, as recited in claim 3, further comprising said sensor being fabricated with integrated circuit processing techniques.

5. The thin film bulk acoustic wave sensor, as recited in claim 4, further comprising:
   said top electrode being positioned adjacent to said active layer; and said top electrode and said active layer array being stacked on said transducer.

6. The thin film bulk acoustic wave sensor, as recited in claim 5, further comprising:
said top electrode being subdivided into a plurality of electrodes;
said active layer being subdivided into a bio-active and chemically active array;
said plurality of electrodes being interspersed with, and laterally adjacent to, said bio-active and chemically active array;
said plurality of electrodes and said bio-active and chemically active array being stacked on said transducer; and
said sensor being a multiple channel thin film bulk acoustic wave sensor.

7. The thin film bulk acoustic wave sensor, as recited in claim 4, further comprising:
said active layer being stacked on said top electrode; and
said sensor being a single channel thin film bulk acoustic wave sensor.

8. A multiple channel thin film bulk acoustic wave sensor, comprising:
a plurality of top electrodes and a bio-active and chemically active array are positioned on a piezo-active thin film transducer;
said plurality of electrodes being interspersed with, and laterally adjacent to, said array;
said transducer being placed on a bottom electrode that is stacked on a substrate with a top surface;
said array contacts a concentration of unknown substances and produces a low-voltage, thickness-direction electric field that excites an extensional plane bulk acoustic wave;
said extensional plane bulk acoustic wave propagates away from said top surface, produces a phase progression substantially oblique to said top surface and simultaneously discriminates against a plurality of nonspecific binding modes from said concentration; and
said plurality of nonspecific modes and said plurality of identification materials identify said concentration.

9. The multiple channel thin film bulk acoustic wave sensor, as recited in claim 8, further comprising:
said array of biological and chemical identification materials being selected from the group consisting of carbon and polymer based bio-active materials, fluorescin-doped antibodies, oligonucleotides and enzymes; and
said substrate being composed of an inert material.

10. The multiple channel thin film bulk acoustic wave sensor, as recited in claim 9, further comprising said sensor being fabricated with integrated circuit processing techniques.

11. The multiple channel thin film bulk acoustic wave sensor, as recited in claim 10, further comprising said plurality of electrodes having different voltages and electrical phases to produce an oblique component of said extensional plane bulk acoustic wave.

12. The multiple channel thin film bulk acoustic wave sensor, as recited in claim 11, further comprising said array concurrently senses a multitude of antigens and agents.

13. A single channel thin film bulk acoustic wave sensor, comprising:
a first electrode and an active layer are positioned on a piezo-active thin film transducer;
said transducer being placed on a second electrode that is stacked on a substrate with a top surface;
said active layer, having an array of biological and chemical identification materials, contacts a concentration of unknown substances and produces a low-voltage, thickness-direction electric field that excites an extensional plane bulk acoustic wave;
said extensional plane bulk acoustic wave propagates away from said top surface, produces a phase progression substantially oblique to said top surface and simultaneously discriminates against a plurality of nonspecific binding modes from said concentration; and
said plurality of nonspecific modes and said plurality of identification materials identify said concentration.

14. The single channel thin film bulk acoustic wave sensor, as recited in claim 13, further comprising:
said first electrode being a top electrode; and
said second electrode being a bottom electrode.

15. The single channel thin film bulk acoustic wave sensor, as recited in claim 14, further comprising:
said array of biological and chemical identification materials being selected from the group consisting of carbon and polymer based bio-active materials, fluorescin-doped antibodies, oligonucleotides and enzymes; and
said substrate being composed of an inert material.

16. The single channel thin film bulk acoustic wave sensor, as recited in claim 15, further comprising said sensor being fabricated with integrated circuit processing techniques.

17. The single channel thin film bulk acoustic wave sensor, as recited in claim 16, further comprising:
said active layer being subdivided into a bio-active and chemically active array;
said top electrode being positioned adjacent to said array; and
said top electrode and said array being stacked on said transducer.

18. The single channel thin film bulk acoustic wave sensor, as recited in claim 16, further comprising:
said top electrode being positioned adjacent to said active layer; and
said top electrode and said active layer being stacked on said transducer.

19. The single channel thin film bulk acoustic wave sensor, as recited in claim 16, further comprising:
said active layer being stacked on said top electrode; and
said top electrode being stacked on said transducer.

20. The single channel thin film bulk acoustic wave sensor, as recited in claim 19, further comprising said active layer being subdivided into a bio-active and chemically active array.

* * * * *